United States Patent
Hansen

(10) Patent No.: US 8,775,201 B2
(45) Date of Patent: Jul. 8, 2014

(54) DATA LOGGER

(75) Inventor: William J. Hansen, Pewaukee, WI (US)

(73) Assignee: Enthermics Medical Systems, Inc., Menomonee Falls, WI (US)

( * ) Notice: Subject to any disclaimer, the term of this patent is extended or adjusted under 35 U.S.C. 154(b) by 856 days.

(21) Appl. No.: 12/250,281

(22) Filed: Oct. 13, 2008

(65) Prior Publication Data

US 2009/0171693 A1 Jul. 2, 2009

Related U.S. Application Data

(60) Provisional application No. 61/018,372, filed on Dec. 31, 2007.

(51) Int. Cl.
- *G06Q 10/00* (2012.01)
- *G06Q 50/00* (2012.01)
- *A61H 5/00* (2006.01)
- *H05B 1/02* (2006.01)

(52) U.S. Cl.
USPC .............................................. 705/2; 219/413

(58) Field of Classification Search
USPC .............................................................. 705/2
See application file for complete search history.

(56) References Cited

U.S. PATENT DOCUMENTS

| | | |
|---|---|---|
| 6,196,113 B1 | 3/2001 | Yung |
| 6,294,762 B1 | 9/2001 | Faries et al. |
| 6,467,953 B1 | 10/2002 | Faries et al. |
| 6,566,631 B2 | 5/2003 | Faries et al. |
| 6,660,974 B2 | 12/2003 | Faries et al. |
| 6,762,930 B2 * | 7/2004 | Minne' ...................... 361/679.55 |
| 6,768,085 B2 | 7/2004 | Faries et al. |
| 7,041,941 B2 * | 5/2006 | Faries et al. .................... 219/413 |
| 7,276,675 B2 | 10/2007 | Faries et al. |
| 7,364,657 B2 | 4/2008 | Mandrusov et al. |
| 2001/0042743 A1 | 11/2001 | Faries et al. |
| 2002/0021741 A1 | 2/2002 | Faries et al. |
| 2002/0024990 A1 | 2/2002 | Faries et al. |
| 2002/0034212 A1 | 3/2002 | Faries et al. |
| 2002/0065685 A1 | 5/2002 | Sasaki et al. |
| 2002/0158058 A1 | 10/2002 | Faries et al. |

(Continued)

FOREIGN PATENT DOCUMENTS

| | | |
|---|---|---|
| DE | 1182734 | 12/1964 |
| DE | 3311805 | 10/1984 |

(Continued)

OTHER PUBLICATIONS

Non-Final Office Action for U.S. Appl. No. 12/343,162 dated Jul. 23, 2010, 11 pages.

(Continued)

*Primary Examiner* — Hiep V Nguyen
(74) *Attorney, Agent, or Firm* — Boyle Fredrickson, S.C.

(57) ABSTRACT

A data logging module and a method of monitoring a medical warming cabinet is disclosed. A temperature of the heating chamber and a state of a door of the heating chamber are sampled at predetermined intervals and recorded as data packets on a memory device. A display may provide a message when the memory device is reaching capacity. Moreover, a selected of the data packets may be analyzed (such as the data packets excluding the data packets when the door is open) for the generation of a report. The data packets from the memory device may be transferred from the memory device to an external memory device as necessary.

16 Claims, 4 Drawing Sheets

(56) References Cited

U.S. PATENT DOCUMENTS

| | | |
|---|---|---|
| 2003/0000939 A1 | 1/2003 | Faries et al. |
| 2003/0030731 A1 | 2/2003 | Colby |
| 2004/0170409 A1 | 9/2004 | Faries, Jr. et al. |
| 2004/0188409 A1 | 9/2004 | Faries et al. |
| 2004/0240520 A1 | 12/2004 | Faries et al. |
| 2004/0247016 A1 | 12/2004 | Faries et al. |
| 2005/0240689 A1* | 10/2005 | Leaming .................. 710/52 |
| 2006/0291533 A1 | 12/2006 | Faries et al. |
| 2007/0000910 A1 | 1/2007 | Faries et al. |
| 2007/0015975 A1 | 1/2007 | Faries et al. |
| 2007/0093786 A1 | 4/2007 | Goldsmith et al. |
| 2007/0115808 A1 | 5/2007 | Ying |
| 2007/0142773 A1 | 6/2007 | Rosiello et al. |
| 2007/0155424 A1 | 7/2007 | Gasper et al. |
| 2008/0205481 A1 | 8/2008 | Faries et al. |

FOREIGN PATENT DOCUMENTS

| | | |
|---|---|---|
| DE | 4019395 | 12/1991 |
| DE | 10058412 | 6/2002 |
| DE | 102004007227 A1 | 8/2007 |
| EP | 1182734 | 2/2002 |

OTHER PUBLICATIONS

Final Office action for U.S. Appl. No. 12/343,162 which is a continuation application of this application, mailed Jan. 20, 2011, 4 pages.

* cited by examiner

DATA LOGGER

CROSS-REFERENCE TO RELATED APPLICATIONS

This application claims the benefit of provisional patent application Ser. No. 61/018,372 entitled "CONTROLLER FOR MEDICAL WARMING CABINETS" filed on Dec. 31, 2007. The content of that application is hereby incorporated by reference as if set forth in its entirety herein.

STATEMENT REGARDING FEDERALLY SPONSORED RESEARCH

Not applicable.

BACKGROUND OF THE INVENTION

This invention is directed at medical warming cabinets. In particular, this invention is directed at a data logging module for a medical warming cabinet and a method of monitoring a medical warming cabinet.

Medical warming cabinets may be used to warm blankets, fluids, and the like. Commonly, medical warming cabinets include one or more compartments that are accessible through a door. Each compartment is heated by at least one heating element that is operated by a controller. In typical operation, the door is open, the items to be heated are placed on structures inside the compartment, the door is closed, and the items are retained in the compartment for a period of time while they are heated.

Medical warming cabinets must operate under the proper temperatures and parameters to avoid overheating and/or spoilage of the items being heated. To this end, the controllers are often programmed to keep each of the compartments within a particular temperature range and alert the user if there has been non-compliance with the desired heating treatment. The user can control the temperature and/or thermal treatment parameters in the cabinet via a user interface such as a control panel.

However, there may be temporary disruptions in temperature that do not significantly impact the thermal treatment of the items. For example, the door to the chamber could be opened, causing a temporary outflux of heated air that causes the temperature in the compartment to quickly drop. Yet, the items being heated may substantially retain their temperature and stay within a usable range.

Further, medical warming cabinets are not well adapted to provide thermal treatment information back to the user. Due to cost limitations and the desire to keep the user interface as simple as possible, the control panel for most medical warming cabinets is small and limited in function. Most medical warming cabinets are limited to providing current temperature, set point information, and the minimum and maximum temperature range information. Even then, in most cabinets, a single display screen must be used to toggle between each of these values.

Hence, there is a need for improved monitoring, recordation, and analysis of thermal treatment information for medical warming cabinets.

BRIEF SUMMARY OF THE INVENTION

A method of monitoring a medical warming cabinet is disclosed. The medical warming cabinet includes a heating chamber heated by a heating apparatus. Access to the heating chamber is provided through a door into the heating chamber. The method includes sampling a temperature of the heating chamber at predetermined intervals and a state of the door. The temperature, the state of the door, and a time of the sampling is recorded in a data packet on a memory device. A message is provided indicating when the memory device is reaching capacity prior to the memory device reaching capacity.

In another form, the disclosed method also includes the steps of sampling a temperature of the heating chamber at predetermined intervals and a state of the door and recording the temperature, the state of the door, and a time of the sampling in a data packet on a memory device. A selected plurality of the data packets excluding data packets within a predetermined time after the door indicates the door is open are analyzed. A report is generated summarizing the analysis of the selected plurality of the data packets.

A data logging module for a controller in a medical warming cabinet is also disclosed. The medical warming cabinet includes a heating chamber heated by a heating apparatus. Access to the heating chamber is provided through a door into the heating chamber. The data logging module includes a temperature sensor sampling a temperature in the heating chamber; a door sensor sampling a state of the door; a memory device recording the temperature, the state of the door, and a time of the sampling in a data packet at a predetermined interval; and a display that displays a message indicating that the memory device is reaching capacity prior to the memory device reaching capacity.

The data obtained may be transferred to an external memory device. This may be performed, for example, using a bus port, such as a USB port to transfer data from the memory device to a removable external memory device such as a USB flash memory drive. In this way, as the memory device in the medical warming cabinet approaches capacity, the data packets can be transferred and stored in a separate system, such as, for example, a personal computer. Moreover, the data can be analyzed to provide reports including the most relevant data.

Additionally, this added functionality can be made with only minor additions to the control panel. Thus, the control panel can remain simple to use and inexpensive to produce, while the medical warming cabinet offers advanced features related to monitoring, recording, and analyzing the thermal treatment of the items contained therein.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION OF THE PREFERRED EMBODIMENTS

Figure 1:
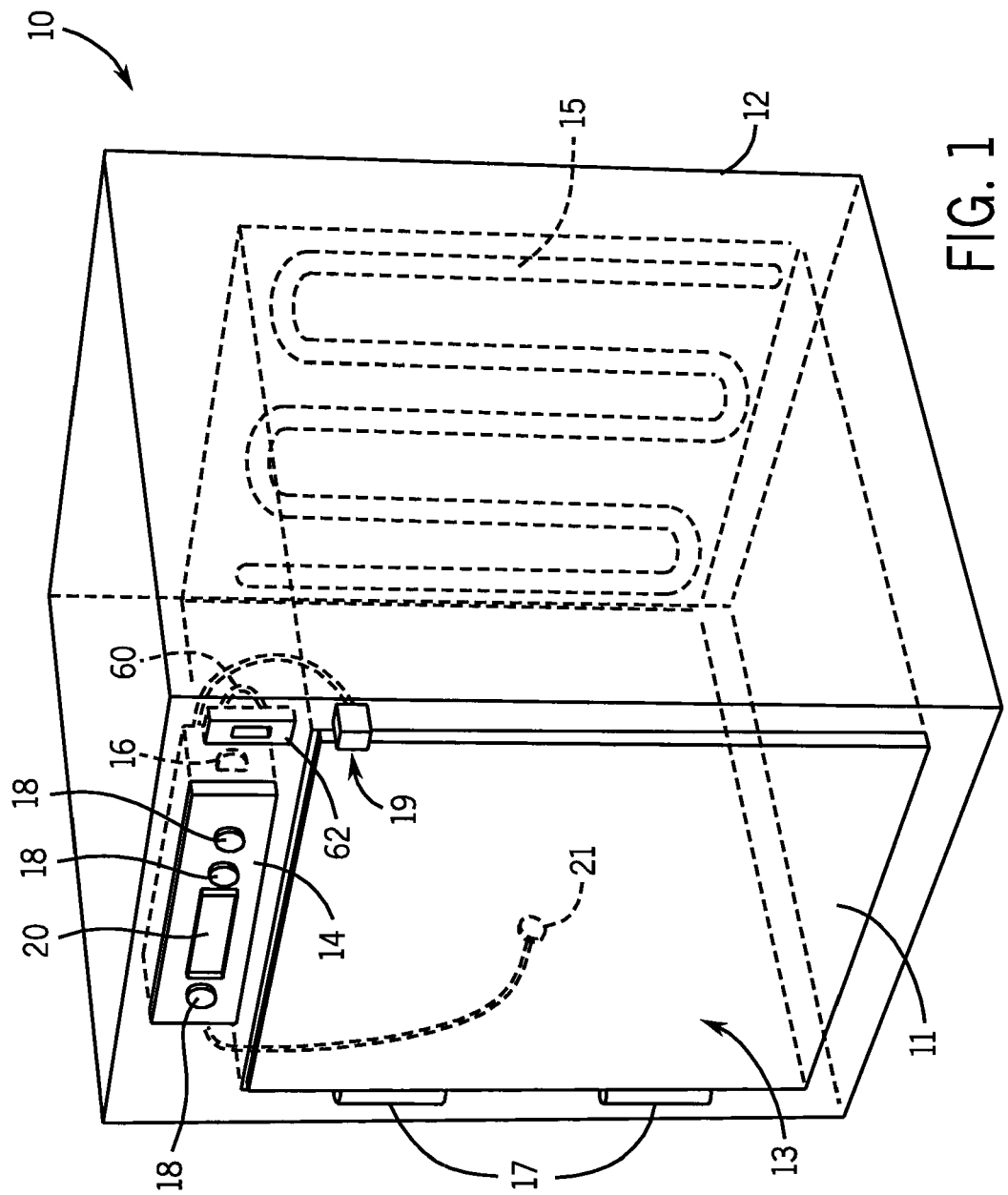
FIG. 1 is a perspective view of a medical warming device with a controller including a removable memory module.

Referring now to FIG. 1, a medical warming cabinet 10 includes a door 11 and walls 12 that define a compartment or heating chamber 13. The heating chamber 13 receives and warms medical items, such as blankets, fluids, and the like.

The door 11 provides access to the heating chamber 13. As shown, the door 11 is hinged to the walls 12 by hinges 17. A door sensor 19 is present that detects whether the door 11 is open or shut. The door sensor 19 may be any kind of sensor including, but not limited to, a mechanical button, switch, or lever that is depressed when the door 11 is closed, an optical sensor, an electrical sensor, a magnetic sensor, and the like.

A heating apparatus 15 heats the heating chamber 13 and is controlled by a controller 14. The heating apparatus 15 can be a heating element, with or without a heat circulating fan, or a low-heat-density electrothermal cable or pad array that is mounted against the inside or outside of the walls 12 define the chamber 13.

The controller 14 is configured to operate the heating apparatus 15 at a particular temperature that is selected by a user. The controller 14 is connected to the door sensor 19 and a temperature sensor 21 for measuring the temperature of the heating chamber 13. Although the temperature sensor 21 is shown as being placed on a side wall of the heating chamber 13, it may be placed in any one of a number of positions within the heating chamber 13.

The controller 14 is connected to the removable storage device 16. Preferably, the removable storage device 16 is not accessible external to the exterior 12 without disassembling the cabinet 10. The controller 14 includes a plurality of operator inputs 18 and a display 20. The controller 14 can be configured differently depending on the information stored on removable storage device 16.

The removable storage device 16 includes information for the operation of the cabinet 10. The information can be stored in a configuration file format. The information can include model, serial, and software version information. The information can include software versions and heating control algorithm information such as allowable temperature ranges and proportional-integral-derivative controller (PID controller) parameters.

For fluid warming cabinets, the controller can be configured to allow for individual temperature controls for irrigation fluids (IRR) and injection fluids (INJ). For example, the IRR temperature can be adjusted within a first range and the INJ temperature can be set within a second range, which is typically lower than the IRR range. The appropriate range of temperatures is available automatically once a user selects the type of fluids to be warmed. The user can then input a setpoint within the range of temperatures. Furthermore, fluid warming cabinets can include an alarm that indicates when a temperature exceeds a temperature that is a certain amount higher than the set temperature. Fluid warming cabinets may include a fan for air-mixing to enhance temperature accuracy.

The information in the configuration file stored on the removable storage device 16 can include the type of warmer, the model number, the serial number, the year of manufacturing, the month of manufacturing, the date of manufacturing, the type of warmer (i.e., blanket or fluid), the injection fluids warming minimum temperature, the injection fluids maximum temperature, the irrigation fluids minimum temperature, the irrigation fluids maximum temperature, the blanket minimum temperature, the blanket maximum temperature, PID integration compensation term normalized to 150 degrees F., PID "D" term normalized to 150 degrees F., PID "I" term normalized to 150 degrees F., PID "P" term normalized to 150 degrees F.; PID "D" sampling period in half seconds, check door sensor enable; the frequency of any data collection module, the number of temperature sensors, the output type (e.g., solid state relay or mechanical relay), and control limits for the relay on each side of the setpoint. The temperature parameters can be in Fahrenheit or Celsius.

The controller 14 is further configured to be replaceable, so that if the controller 14 fails, the controller 14 can be removed from the warming cabinet 10 and replaced with a new controller. The controller 14 can be configured to be replaceable through the use of removable connectors and lines that connect the controller 14 to the other components of the cabinet 10, such as a power supply, relays, the heating apparatus, and sensors. Because the removable memory device 16 can be removed from the controller 14 that is being replaced, the removable memory device 16 can be easily inserted into the new controller. Accordingly, the new controller is configured to operate exactly like the failed controller without having to tediously input the control parameters by using the user inputs and without requiring a specialized programming device. Furthermore, the controller 14 can be updated simply by removing an old removable storage device and either updating the old device or inserting a new removable storage device 16 including the updated information. Once the new removable memory device is installed in the controller, the controller 14 loads the information, such as by loading a configuration file, from the removable memory device 16. In this way, the controller 14 can be also be easily updated.

For clarity, the removable storage device 16 is not the same as the external memory device that will be described later with respect to the data logging module. The removable storage device 16 is designed to be permanently retained in the controller 14, except when, for example, replacing a faulty controller or upgrading the information for operation of the cabinet 10. As described above, this typically involves disassembly of the cabinet 10. In contrast, the external memory device is for offloading data from the cabinet 10, such as information that has been recorded pertaining to the operation of the cabinet 10. As will be described below, this periodic transferring of data is intended to be easy accessible by the user.

Figure 2:
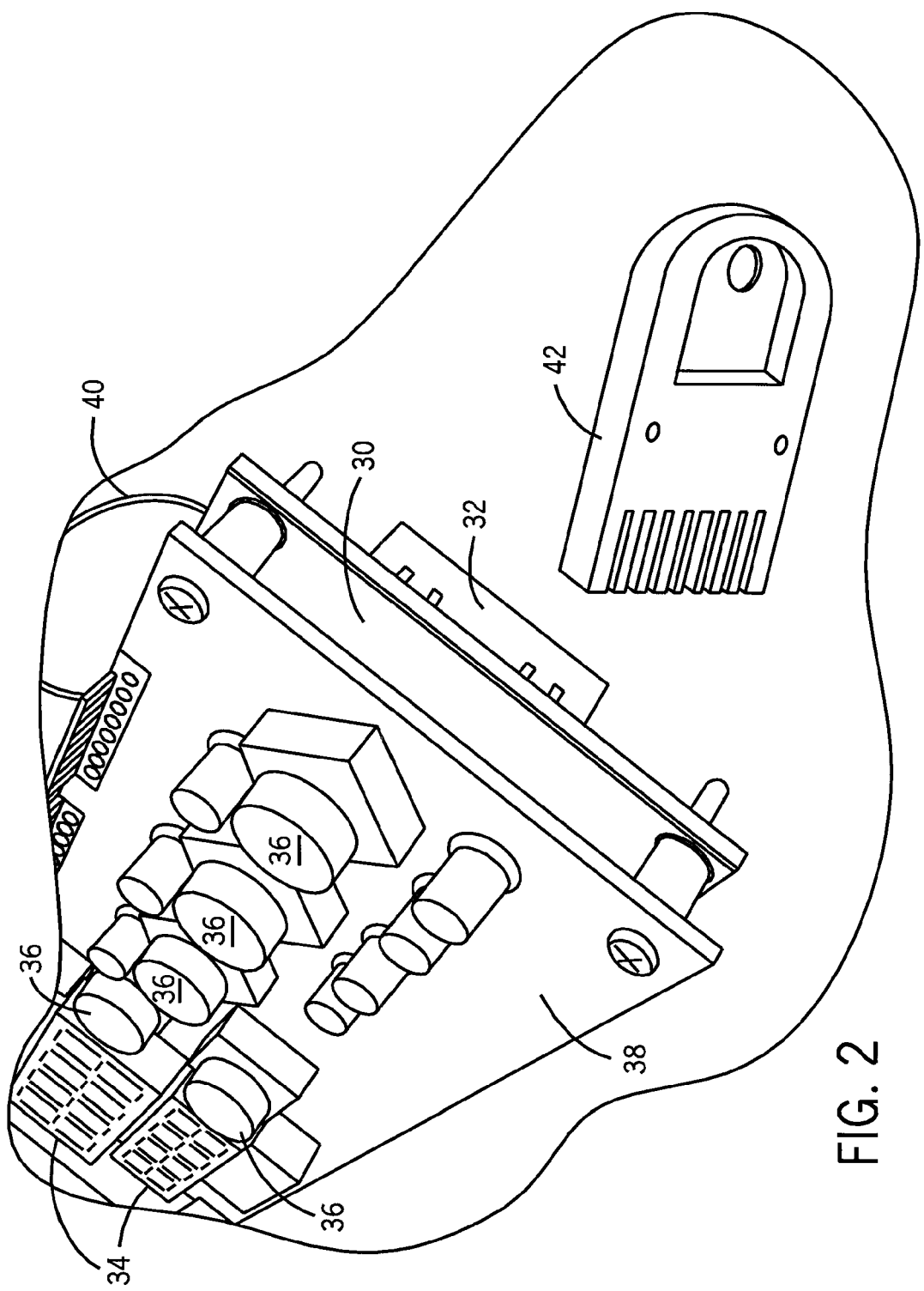
FIG. 2 is a perspective view of a medical warming device controller with a removable memory device that has been removed.
Figure 3:
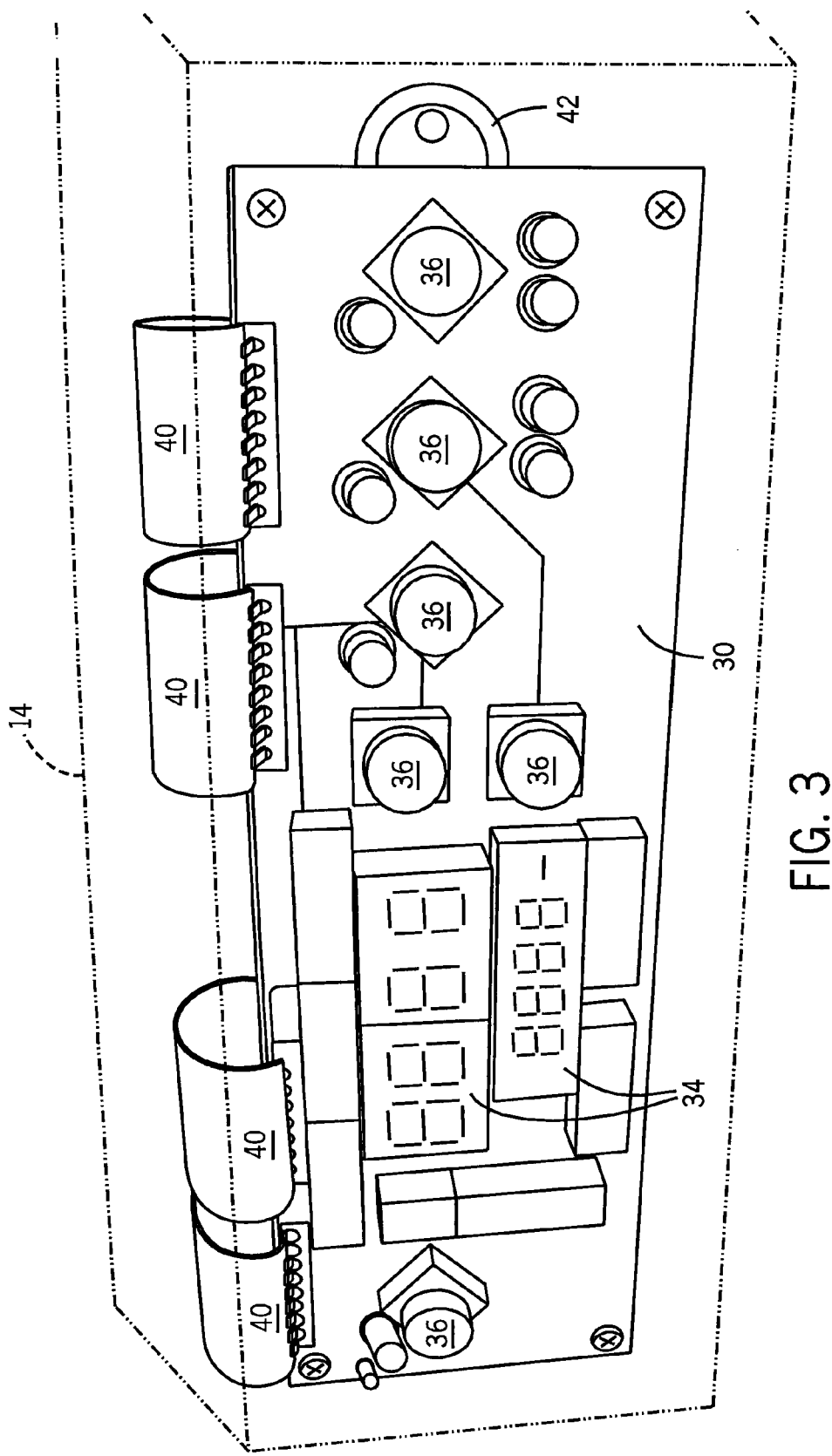
FIG. 3 is a perspective view of a medical warming device controller with a removable memory device that has been installed.

FIGS. 2 and 3 show a controller 30 for use with a medical warming cabinet. The controller 30 includes a removable memory socket 32, user display 34, user inputs 36, LEDs 38, and a plurality of connectors 40 for connection to other components of a warming cabinet. In FIG. 2, a removable memory device 42 is shown removed from the removable memory socket 32. In FIG. 3, the removable memory device 42 is shown inserted into the removable memory socket 32, which can be a bus port. The removable memory device 42 can be a memory chip, memory stick, memory card, and the like. The removable memory socket 32 is configured to allow for the information stored on the removable memory device 42 to be loaded by controller 30. The controller 30 can comprise a plurality of printed circuit boards including a processor, memory, buses, communication lines, and other electrical components as is well understood in the art.

Figure 4:
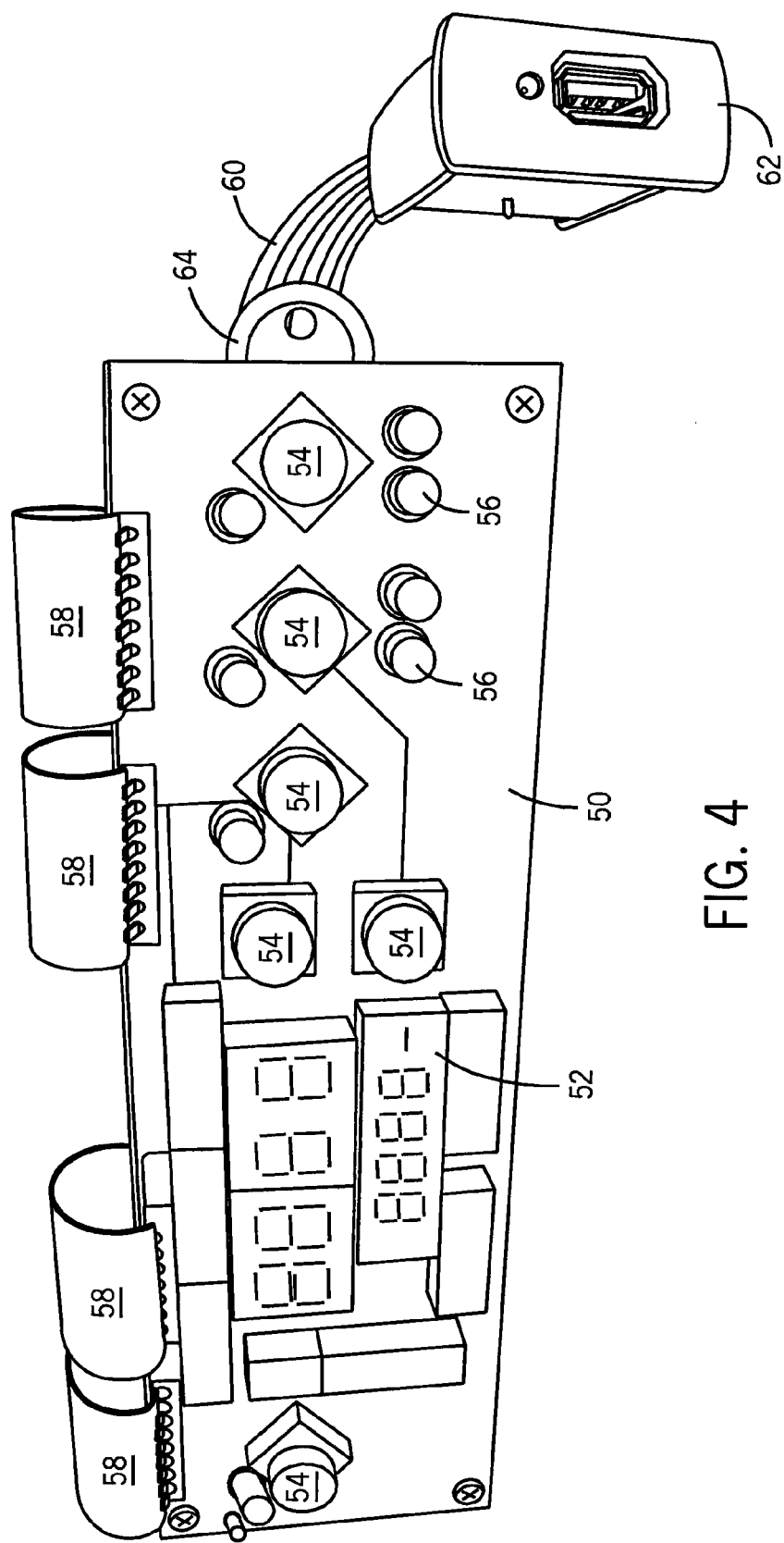
FIG. 4 is a perspective view of a medical warming device controller with a removable memory device that has been installed and a bus port.

FIG. 4 shows a controller 50 for use with a medical warming cabinet. As discussed in more detail below, the controller 50 includes a processor and memory device configured to operate as a data logging module. The memory device may be a portion of the removable storage device 16, memory onboard the controller, or any other type of memory storage. Controller 50 includes a display 52, user inputs 54, LEDs 56, and a plurality of connectors 58 for connection to other components of a warming cabinet. The controller 50 can comprise a plurality of printed circuit boards including a processor, memory, buses, communication lines, and other electrical components as is well understood in the art. Controller 50 is connected by bus lines 60 to a bus port 62, which is configured to receive a data logging memory device (not shown) that can be read/written by the controller 30. In one embodiment, bus port 62 is a universal serial bus (USB) port and memory device is a USB flash drive. Bus port 62 is disposed on the warmer to be conveniently accessible without disassembling the warmer in which it is installed. Controller 50 can also include a removable control memory socket/port (not shown) configured to accept a removable control memory device 64, which in FIG. 4 is shown inserted into the removable memory socket.

The data logging module of the controller 50 is configured to log (i.e., sample and record) operational data by sampling data at a predetermined sample rate and storing data packets for each sample. The data packets can include a time/date stamp, the current set point for the warmer compartment, a first measured temperature of the compartment provided by a first temperature sensor (such as temperature sensor 21), a second measured temperature of the compartment provided by a second temperature sensor, a state of a door sensor 19 on the warmer, the warmer type, and error logging. All data sampling packets for temperature can be taken from the first sensor 21, but a preferred method is to have an additional sensor and circuitry for independent reporting of the warmer function. In an embodiment, the data packets are sampled at a rate of one per hour and are stored in a memory sized to store six months of data.

In one embodiment, the memory device is a circular memory buffer. As the operational information is sampled and recorded, the data packets are stored in the circular memory buffer and, when the memory is full, the oldest of the data packets are overwritten during the step of recording.

The controller 50 can be configured to use the display 52 to indicate that the data logging memory is full and a download is required or as the memory device is reaching capacity. In one embodiment, a message, such as the word "full", can flash alternately with a displayed temperature of the compartment. When a data logging memory device or external memory device is inserted into the bus port 62, the controller 50 automatically transfers the logged data to the data logging memory device. The controller 50 indicates on display 52 that the data is being downloaded to the data logging memory device and also indicates when the download has completed. In an embodiment, the display 52 shows "USB DMP" during the download and "USB DONE" once the download has completed and until the data logging memory device has been removed. Once the data logging memory device has been removed, the display function is returned to normal operation. The data can be written to the data logging memory device in a comma delimited format or summarized in a report having. In one embodiment, the user inputs 54 are not locked out when the data is being downloaded.

The controller 50 can be configured to summarize the logged data in a report format. The report format can be configured to exclude samples that were taken, for example, within two hours of when the door was open or, according to another example, within two hours of when the warmer was turned on. Of course, two hours is only one example and other lengths of time could be selected when determining which samples to exclude from the report. The report can be a text file including the following information: model number, serial number, date of manufacture of unit, date of report/download, software version, frequency a reading was taken, separate report sections for each set point, units, warmer mode, or month change of greater than eight valid readings, and an overall statement summarizing the accuracy of the data and indicating how the data was collected. The separate report section for each set point, units, warmer mode, or month change of greater than eight valid readings including the following information: period of accuracy the section covers, number of days the section covers, number of readings evaluated for the accuracy calculation, number of readings excluded from the accuracy calculation due to the door being opened within a specified time of a reading, mode of warming, warmer accuracy specification, warmer setpoint temperature, average temperature, temperature range, and accuracy evaluation statement indicating if the unit passed or failed to meet the specified accuracy at the selected set point.

The controllers of the present invention can be set by a user to operate in Fahrenheit and Celsius and allows a user to input a temperature within a range of temperatures. The controllers can include a timer that allows a user to control when the cabinet turns on and off. The controllers can also have a lock-out feature and a series of prompt sequence indicators. The controllers can also control interior lighting. The cabinet can include a warming shut-off system that is separate from controller and is configured to prevent overheating.

A warmer can include two compartments that are warmed separately, which allows for flexibility in choosing particular temperatures for warmed blankets or warmed fluids. Combination cabinets can include a blanket warming compartment and a fluid warming compartment. The compartments can be controlled by separate controllers. Alternatively, a single controller can be configured to control more than one compartment.

While there have been shown and described what is at present considered the preferred embodiments of the invention, it will be obvious to those skilled in the art that various changes and modifications can be made therein without departing from the scope of the invention defined by the appended claims.

What is claimed is:

1. A method of monitoring a medical warming cabinet employing a computer and a door sensor, the medical warming cabinet including a heating chamber heated by a heating apparatus, access to the heating chamber provided through a door into the heating chamber, and an electronic temperature monitoring system, the method comprising:
   receiving an electrical output from the door sensor at the temperature monitoring system indicating that the door into the heating chamber has been moved from a closed position into an open position;
   determining a door open time based on receipt of the door open status signal;
   receiving a temperature value at the temperature monitoring system from a temperature sensor configured to determine a temperature of the heating chamber at a temperature sensing time;
   recording in a data packet on a memory device the temperature value, the temperature sensing time, and the door open time that is proximate and prior to the temperature sensing time;
   analyzing a selected plurality of data packets rejecting data packets where the temperature sensing time is within a defined time limit of the door opening time; and
   generating a report providing temperature information based on at least one temperature value selected according to the temperature sensing time and the door open time wherein temperature values taken within the defined time limit of the door opening time are rejected to preferentially differentiate temperature values taken when the door is closed.

2. The method of claim 1, wherein the data packets are stored in a circular memory buffer and, when the memory is full, an oldest of the data packets are overwritten during the step of recording.

3. The method of claim 1, wherein the temperature is sampled at a predetermined rate of one sample per hour to generate the temperature value.

4. The method of claim 3, wherein the step of sampling further includes sampling a set point for the heating chamber, a warmer type, and an error status.

5. The method of claim 1, further comprising: transferring the data packets from the memory device to an external memory device.

6. The method of claim 5, wherein the step of transferring the data packets from the memory device to an external memory device includes inserting a removable external memory device into a bus port on the medical warming cabinet.

7. The method of claim 6, wherein the removable external memory device is a USB flash memory drive.

8. The method of claim 6, wherein the transfer of the data packets from the memory device to the external memory device occurs automatically upon insertion of the removable memory device into the bus port.

9. The method of claim 5, wherein the step of transferring the data packets from the memory device to the external memory device further comprises generating a report summary and writing the report summary to the device.

10. A method of monitoring a medical warming cabinet employing a computer and a door sensor, the medical warming cabinet including a heating chamber heated by a heating apparatus, access to the heating chamber provided through a door into the heating chamber, and an electronic temperature monitoring system, the method comprising:
   receiving an electrical output from the door sensor at the temperature monitoring system indicating that the door into the heating chamber has been moved from a closed position into an open position;
   determining a door open time based on receipt of the door open status signal;
   receiving a temperature value at the temperature monitoring system from a temperature sensor configured to determine a temperature of the beating chamber at a temperature sensing time;
   recording in a data packet on a memory device the temperature value, the temperature sensing time, and an associated door open time that is proximate and prior to the temperature sensing time;
   analyzing a selected plurality of data packets rejecting data packets where the temperature sensing time is within a defined time limit of the door opening time; and
   generating a report providing temperature information derived from one or more recorded temperature values from the memory device, the one or more recorded temperature values excluding temperature values having a temperature sensing time that is within a defined time limit of the associated door opening time to preferentially differentiate temperature values taken when the door is closed such that the temperature information would be substantially affected by loss of heat through the opening door.

11. A method of claim 10, further comprising providing a message indicating the memory device is reaching capacity prior to the memory device reaching capacity.

12. A data logging module for a controller in a medical warming cabinet, the medical warming cabinet including a heating chamber heated by a heating apparatus, access to the heating chamber provided through a door into the heating chamber, the data logging module comprising:
   a temperature sensor configured to periodically determine a temperature value for the heating chamber;
   a door sensor configured to detect that the door into the heating chamber has been moved from a closed position into an open position;
   a memory device; and
   an electronic temperature monitoring system configured to
      receive an electrical output from the door sensor indicating that the door into the heating chamber has been moved from a closed position into an open position,
      generate a door open time when the electrical output is received from the door sensor indicating that the door into the heating chamber has been moved from a closed position into an open position,
      periodically generate a temperature value based on data received from the temperature sensor, associate a temperature time with the temperature value, analyze a selected plurality of data packets rejecting data packets where the temperature sensing time is within a defined time limit of the door opening time, and generate a report including the temperature value, the temperature sensing time, and the door open time that is proximate and prior to the temperature sensing time, the report providing temperature information based on at least one temperature value selected according to the temperature sending time and the door open time wherein temperature values taken within the defined time limit of the door opening time are rejected to preferentially differentiate temperature values taken when the door is closed.

13. The data logging module of claim 12, wherein the memory device has a circular memory buffer.

14. The data logging module of claim 12, further comprising a bus port for receiving an external memory device for storing the data.

15. The data logging module of claim 14, wherein the external memory device for storing the data is a USB flash memory drive.

16. The data logging module of claim 14, wherein the temperature monitoring system is further configure to generate a temperature value report excluding data where the temperature sensing time is within a defined time limit of the door opening time.

* * * * *